United States Patent
Le et al.

(10) Patent No.: US 10,851,049 B2
(45) Date of Patent: Dec. 1, 2020

(54) CURABLE BENZOXAZINE COMPOSITIONS

(71) Applicant: HUNTSMAN ADVANCED MATERIALS AMERICAS LLC, The Woodlands, TX (US)

(72) Inventors: Dong Le, Richmond, TX (US); Derek Kincaid, Spring, TX (US); Dong Wang, The Woodlands, TX (US); Bradley Rechichar, The Woodlands, TX (US)

(73) Assignee: HUNTSMAN ADVANCED MATERIALS AMERICAS LLC, The Woodlands, TX (US)

(*) Notice: Subject to any disclaimer, the term of this patent is extended or adjusted under 35 U.S.C. 154(b) by 0 days.

(21) Appl. No.: 15/877,063

(22) PCT Filed: Jul. 20, 2016

(86) PCT No.: PCT/US2016/043144
§ 371 (c)(1),
(2) Date: Jan. 22, 2018

(87) PCT Pub. No.: WO2017/015376
PCT Pub. Date: Jan. 26, 2017

(65) Prior Publication Data
US 2018/0186730 A1    Jul. 5, 2018

Related U.S. Application Data

(60) Provisional application No. 62/195,944, filed on Jul. 23, 2015.

(51) Int. Cl.
| | | |
|---|---|---|
| *C07C 265/16* | (2006.01) | |
| *C08J 5/24* | (2006.01) | |
| *C08G 73/10* | (2006.01) | |
| *C08G 59/40* | (2006.01) | |
| *C08G 59/00* | (2006.01) | |
| *C08L 63/00* | (2006.01) | |
| *C08G 59/42* | (2006.01) | |
| *C08L 63/10* | (2006.01) | |
| *C08L 79/08* | (2006.01) | |

(52) U.S. Cl.
CPC ............ *C07C 265/16* (2013.01); *C08G 59/00* (2013.01); *C08G 59/40* (2013.01); *C08G 59/4014* (2013.01); *C08G 59/42* (2013.01); *C08G 73/1007* (2013.01); *C08G 73/1067* (2013.01); *C08J 5/24* (2013.01); *C08L 63/00* (2013.01); *C08L 63/10* (2013.01); *C08J 2379/08* (2013.01); *C08L 79/08* (2013.01)

(58) Field of Classification Search
None
See application file for complete search history.

(56) References Cited

U.S. PATENT DOCUMENTS

| | | | |
|---|---|---|---|
| 3,856,752 | A | 12/1974 | Bateman et al. |
| 4,607,091 | A | 8/1986 | Schreiber et al. |
| 4,692,272 | A | 9/1987 | Goswami et al. |
| 5,021,484 | A | 6/1991 | Schreiber et al. |
| 5,200,452 | A | 4/1993 | Schreiber |
| 5,200,454 | A | 4/1993 | Nakano |
| 5,443,911 | A | 8/1995 | Schreiber et al. |
| 5,543,516 | A | 8/1996 | Ishida |
| 2006/0069088 | A1 | 3/2006 | Goble et al. |
| 2010/0261395 | A1 | 10/2010 | Lehmann et al. |
| 2011/0189458 | A1 | 8/2011 | Sudo et al. |

FOREIGN PATENT DOCUMENTS

| | | | |
|---|---|---|---|
| EP | 1639038 A1 | 3/2006 | |
| EP | 2736999 B1 | 7/2018 | |
| JP | 2003275773 A1 | 9/2003 | |
| JP | 2005272722 A1 | 10/2005 | |
| JP | 4455114 B2 * | 4/2010 | |
| WO | 2005000955 A1 | 1/2005 | |
| WO | 2007064801 A1 | 6/2007 | |
| WO | 2009075744 A2 | 6/2009 | |
| WO | 2009075746 A2 | 6/2009 | |
| WO | 2010031826 A1 | 3/2010 | |
| WO | 2012015604 A1 | 2/2012 | |
| WO | 2012100980 A1 | 8/2012 | |
| WO | 2013122800 A1 | 8/2013 | |
| WO | 2014137717 A1 | 9/2014 | |
| WO | 2015130464 A1 | 9/2015 | |
| WO | 2006028672 A2 | 3/2016 | |
| WO | 2016099922 A2 | 6/2016 | |

OTHER PUBLICATIONS

JP 4455114 B2 machine translation (2010).*
PCT International Search Report and the Written Opinion of the International Searching Authority dated Dec. 8, 2016, for patent application PCT/EP2016/043144, filed Jun. 20, 2016, 15 pages.

* cited by examiner

*Primary Examiner* — Ana L. Woodward
(74) *Attorney, Agent, or Firm* — Huntsman Advanced Materials Americas LLC; Lewis Craft

(57) ABSTRACT

The present disclosure provides a curable composition containing a benzoxazine, reactive diluent and a soluble polyimide. The curable composition, upon curing, renders an article having well balanced thermal, chemical and mechanical properties and may be used in a variety of applications, such as in coatings, structural composites and encapsulating systems for electronic and electrical components.

11 Claims, No Drawings

CURABLE BENZOXAZINE COMPOSITIONS

CROSS-REFERENCE TO RELATED APPLICATION

This application is the National Phase of International Application PCT/US2016/043144 filed Jul. 20, 2016 which designated the U.S. and which claims priority to provisional Application Ser. No. 62/195,944 filed Jul. 23, 2015. The noted applications are incorporated herein by reference.

STATEMENT REGARDING FEDERALLY SPONSORED: RESEARCH OR DEVELOPMENT

Not applicable.

FIELD OF INVENTION

This disclosure relates to a curable composition containing a benzoxazine, a reactive diluent and a soluble polyimide. The curable composition is useful in a variety of applications, such as in an adhesive, sealant, coating, structural or non-structural composite and encapsulating system for electronic and electrical components.

BACKGROUND OF THE INVENTION

Polymers derived from the ring opening polymerization of benzoxazines compete with phenolic, epoxy and other thermoset or thermoplastic resins in various applications, such as in prepregs, laminates, PWB's, molding compounds, sealants, sinter powders, cast articles, structural composites and electrical components. The benzoxazines, which are synthesized by reacting a phenol with an amine and an aldehyde in the presence or absence of a solvent, have been shown to be, upon curing, dimensionally stable with good electrical and mechanical resistance, low shrinkage, low water absorption and to have medium to high glass transition temperatures.

Benzoxazines have also been combined with various epoxy resins to produce curable compositions (see for e.g. U.S. Pat. No. 4,607,091 (Schreiber), U.S. Pat. No. 5,021,484 (Schreiber), U.S. Pat. No. 5,200,452 (Schreiber) and U.S. Pat. No. 5,443,911 (Schreiber)). Because the epoxy resin reduces the melt viscosity of the benzoxazine, these blends have been shown to be useful in electrical applications since they are able to handle higher filler loadings while still maintaining a processable viscosity. One drawback to the use of such blends, however, is that higher curing temperatures are usually necessary. Furthermore, although these blends exhibit high glass transition temperatures after curing, toughness and stiffness are usually sacrificed to some degree.

More recently, tougheners have been added to improve flexibility. For example, WO 2014/137717 (Wang et al.) discloses the use of a polysulfone based-toughener for a benzoxazine-based composition; WO 2010/031826 (Kreiling et al.) discloses curable compositions that contain a benzoxazine compound and a phenol (preferably bisphenol-A) end-capped prepolymer toughener; EP 1639038B1 (Lei et al.) discloses a curable composition containing a benzoxazine and an acrylonitrile-butadiene copolymer toughener; WO 2009/075746 (Taden et al.) teaches curable compositions that include a benzoxazine and a benzoxazine macromonomer toughener containing at least 3 benzoxazine rings and at least one aliphatic, heteroaliphatic, araliphatic, heteroaralaliphatic, aromatic or heteroaromatic soft fragment; WO 2009/075744 (Kreiling et al.) teaches the use of benzoxazine-based and non-benzoxazine-based toughening additives for a benzoxazine matrix resin component; WO 2007/064801 discloses a composition that contains a benzoxazine and a combination of two adduct tougheners; the first being prepared from hydroxy-containing compounds, isocyanate-containing compounds and a phenolic compound; and, the second being prepared from the first adduct and an epoxy-containing compound and a second phenolic compound; WO 2012/015604 (Tran) discloses a benzoxazine component and a phenol-terminated polyurethane, polyurea or a polyurea-urethane; and WO 2012/100980 (Cross et al.) teaches a composition that includes a benzoxazine component, an arylsulphone-containing benzoxazine component and a polyethersulfone so that a homogeneous miscible blend is obtained.

Notwithstanding the state of the technology, it is an object of the present disclosure to provide an improved benzoxazine-based composition containing a toughening agent which, upon curing, is able to perform thermally, mechanically and physically at high temperatures for long periods of time without sacrificing glass transition temperature, strength, toughness or hydrolytic stability properties, therefore making it useful in high temperature applications within various industries, such as the aerospace, electronic and automotive industries.

SUMMARY OF THE INVENTION

The present disclosure provides a curable composition that includes a benzoxazine, reactive diluent and a soluble polyimide. In one embodiment, the curable composition forms, upon curing, an article having a glass transition temperature greater than 180° C. In another embodiment, the curable composition forms, upon curing, an article having a fracture toughness greater than 200 J/m2, while in still another embodiment the curable composition forms, upon curing, an article having a dry flexural modulus greater than 4000 MPa.

The curable composition according to the present disclosure may be used in a variety of applications such as in a coating, adhesive, sealant and structural or non-structural composite and is therefore useful in various industries, such as in the aerospace, automotive or electronic industries.

DETAILED DESCRIPTION OF THE INVENTION

If appearing herein, the term "comprising" and derivatives, thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical object of the article. By way of example, "a benzoxazine" means one benzoxazine or more than one benzoxazine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phases do not necessarily refer to the same embodiment. If the specification states a component or feature "may", "can", "could", or "might" be included or have a characteristic, that particular component or feature is not required to be included or have the characteristic.

The present disclosure provides a curable composition containing a benzoxazine, a reactive diluent and a soluble polyimide. It has been surprisingly found that this combination of components provides a curable composition that, upon curing, exhibits significant improvement in several critical thermomechanical properties such as fracture toughness, tensile and flexural modulus, glass transition temperature and hydrolytic stability.

According to one embodiment, the curable composition contains a benzoxazine. The benzoxazine, which imparts mechanical strength, low water absorption and thermal curability to the composition, may be any curable monomer, oligomer or polymer containing at least one benzoxazine moiety.

Thus, in one embodiment, the benzoxazine may be represented by the general formula (1):

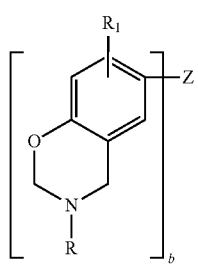

(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and Z is a direct bond (when b=2), a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O. Substituents include, but are not limited to, hydroxy, $C_1$-$C_{20}$ alkyl, a $C_2$-$C_{10}$ alkoxy, mercapto, $C_3$-$C_8$ cycloalkyl, $C_6$-$C_{14}$ heterocyclic, $C_6$-$C_{14}$ aryl, $C_6$-$C_{14}$ heteroaryl, halogen, cyano, nitro, nitrone, amino, amido, acyl, oxyacyl, carboxyl, carbamate, sulfonyl, sulfonamide and sulfuryl.

In a particular embodiment within formula (1), the benzoxazine may be represented by the following formula (1a):

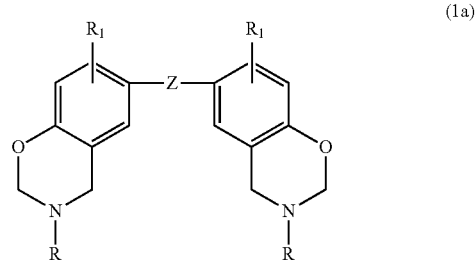

(1a)

where Z is selected from a direct bond, $CH_2$, $C(CH_3)_2$, C=O, O, S, S=O, O=S=O and

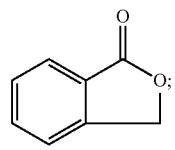

each R is independently hydrogen, a $C_1$-$C_{20}$ alkyl group, an allyl group, or a $C_6$-$C_{14}$ aryl group; and $R_1$ is defined as above.

In another embodiment, the benzoxazine may be represented by the following general formula (2)

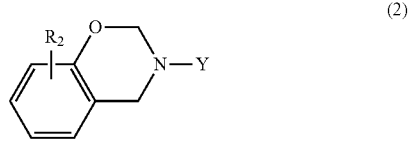

(2)

where Y is a $C_1$-$C_{20}$ alkyl group, a $C_2$-$C_{20}$ alkenyl group, or substituted or unsubstituted phenyl; and $R_2$ is hydrogen, halogen, a $C_1$-$C_{20}$ alkyl group or a $C_2$-$C_{20}$ alkenyl group. Suitable substituents for phenyl are as set forth above.

In a particular embodiment within formula (2), the benzoxazine may be represented by the following formula (2a)

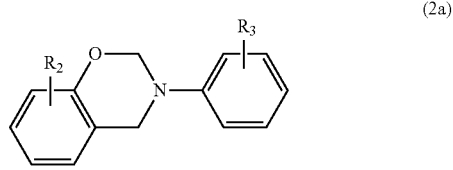

(2a)

where $R_2$ is hydrogen, a $C_1$-$C_{20}$ alkyl or $C_2$-$C_{20}$ alkenyl group, each of which is optionally substituted or interrupted by one or more O, N, S, C=O, COO and NHC=O, and a $C_6$-$C_{20}$ aryl group; and $R_3$ is hydrogen, a $C_1$-$C_{20}$ alkyl or $C_2$-$C_{20}$ alkenyl group, each of which is optionally substituted or interrupted by one or more O, N, S, C=O, COOH and NHC=O or a $C_6$-$C_{20}$ aryl group.

Alternatively, the benzoxazine may be represented by the following general formula

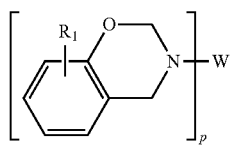
(3)

where p is 2, W is selected from biphenyl, diphenyl methane, diphenyl isopropane, diphenyl sulfide, diphenyl sulfoxide, diphenyl sulfone, and diphenyl ketone, and $R^1$ is defined as above.

In the present disclosure, combinations of multifunctional benzoxazines, combinations of monofunctional benzoxazines, or combinations of one or more multifunctional benzoxazines and one or more monofunctional benzoxazines may be used.

The benzoxazines are commercially available from several sources including Huntsman Advanced Materials Americas LLC and Shikoku Chemicals Corporation.

The benzoxazines may also be obtained by reacting a phenol compound, for example, bisphenol-A, bisphenol-F, phenolphthalein or thiodiphenol, with an aldehyde, for example, formaldehyde, and a primary amine, under conditions in which water is removed. This is further described in U.S. Pat. No. 5,543,516, the contents of which are herein incorporated by reference. The molar ratio of phenol compound to aldehyde reactant may be from about 1:3 to 1:10, alternatively from about 1:4: to 1:7. In still another embodiment, the molar ratio of phenol compound to aldehyde reactant may be from about 1:4.5 to 15. The molar ratio of phenol compound to primary amine reactant may be from about 1:1 to 1:3, alternatively from about 1:1.4 to 1:2.5. In still another embodiment, the molar ratio of phenol compound to primary amine reactant may be from about 1:2.1 to 1:2.2.

Examples of primary amines include: aromatic mono- or diamines, aliphatic amines, cycloaliphatic amines and heterocyclic monoamines; for example, aniline, o-, m- and p-phenylene diamine, benzidine, 4,4'-diaminodiphenyl methane, cyclohexylamine, butylamine, methylamine, hexylamine, allylamine, furfurylamine, ethylenediamine, and propylenediamine. The amines may, in their respective carbon part, be substituted by $C_1$-$C_8$ alkyl or allyl. In one embodiment, the primary amine is a compound having the general formula $R_aNH_2$, wherein $R_a$ is allyl, unsubstituted or substituted phenyl, unsubstituted or substituted $C_1$-$C_8$ alkyl or unsubstituted or substituted $C_3$-$C_8$ cycloalkyl. Suitable substituents on the $R_a$ group include, but are not limited to, amino, $C_1$-$C_4$ alkyl and allyl. In some embodiments, one to four substituents may be present on the $R_a$ group. In one particular embodiment, $R_a$ is phenyl.

According to another embodiment, the benzoxazine may be included in the curable composition in an amount in the range of between about 40% by weight to about 90% by weight, based on the total weight of the curable composition. In another embodiment, the benzoxazine may be included in the curable composition in an amount in the range of between about 50% by weight to about 80% by weight, based on the total weight of the curable composition. In still another embodiment, the benzoxazine may be included in the curable composition at an amount greater than about 40% by weight, while in other embodiments greater than about 50% by weight, based on the total weight of the curable composition. In a further embodiment, the benzoxazine may be included in the curable composition at an amount less than about 90% by weight, while in still other embodiments less than about 80% by weight, based on the total weight of the curable composition, According to another embodiment, the curable composition contains a reactive diluent. As used herein, a "reactive diluent" includes any compound which is completely soluble, reactive and, when combined with the benzoxazine and soluble polyimide, capable of reducing the composition's viscosity.

In one embodiment, the reactive diluent is an epoxy reactive diluent. The epoxy reactive diluent may be a mono-, di- or poly-epoxide and further may be aliphatic, cycloaliphatic or an aromatic compound. The mono-, di- or poly-epoxide may be used alone or in mixtures with one another. The mono-, di- or poly-epoxide may also be pre-cured by chemical means, for example, by reaction with dials or dicarboxylic acid anhydrides.

In another embodiment, the epoxy reactive diluent may be a glycidyl terminated compound, for example, a compound containing a glycidyl or β-methylglycidyl group directly attached to an atom of oxygen, nitrogen, or sulfur. Such epoxy reactive diluents include, but are not limited to, polyglycidyl and poly(β-methylglycidyl) esters obtained by the reaction, of a substance containing two or more carboxylic acid groups per molecule with epichlorohydrin, glycerol dichlorohydrin or β-methylepichlorohydrin in the presence of alkali. The polyglycidyl esters may be derived from aliphatic carboxylic acids, for example, oxalic acid, succinic acid, adipic acid, sebacic acid, or dimerized or trimerized linoleic acid, from cycloaliphatic carboxylic acids such as hexahydrophthalic, 4-methylhexahydrophthalic, tetrahydrophthalic, and 4-methyltetrahydrophthalic acid, or from aromatic carboxylic acids such as phthalic acid, isophthalic acid and terephthalic acid.

Other epoxy reactive diluents which may be used include polyglycidyl and poly(β-methylglycidyl) ethers obtained by the reaction of substances containing per molecule, two or more alcoholic hydroxy groups, or two or more phenolic hydroxy groups, with epichlorohydrin, glycerol dichlorohydrin or β-methylepichlorohydrin, under alkaline conditions or, alternatively, in the presence of an acidic catalyst with subsequent treatment with alkali. Such polyglycidyl ethers may be derived from aliphatic alcohols, for example, ethylene glycol and poly(oxyethylene)glycols such as diethylene glycol and triethylene glycol, propylene glycol and poly(oxypropylene)glycols, propane-1,2-diol, propane-1,3-diol, butane-1,4-diol, pentane-1,5-diol, hexane-1,6-diol, hexane-2,4,6-triol, glycerol, 1,1,1-trimethylolpropane, and pentaerythritol; from cycloaliphatic alcohols, such as quinitol, 1,1-bis(hydroxymethyl)cyclohex-3-ene, bis(4-hydroxycyclohexyl)methane, 1,4-dimethylol-cyclohexane and 2,2-bis(4-hydroxycyclohexyl)-propane; or from alcohols containing aromatic nuclei, such as N,N-bis-(2-hydroxyethyl)aniline and 4,4'-bis(2-hydroxyethylamino)diphenylmethane. In one embodiment, the polyglycidyl ethers are derived from substances containing two or more phenolic hydroxy groups per molecule, for example, resorcinol, catechol, hydroquinone, bis(4-hydroxyphenyl)methane, 1,1,2,2-tetrakis(4-hydroxyphenyl)ethane, 4,4'-dihydroxydiphenyl, bis(4-hydroxyphenyl) sulphone, and especially, phenolformaldehyde or cresol-formaldehyde novolac resins, 2,2-bis(4-hydroxyphenyl)propane (otherwise known as bisphenol A), and 2,2-bis(3,5-dibromo-4-hydroxyphenyl)-propane.

There may further be employed epoxy reactive diluents which include poly(N-glycidyl) compounds, such as are, for example, obtained by the dehydrochlorination of the reaction products of epichlorohydrin and amines containing at least two hydrogen atoms directly attached to nitrogen, such as aniline, n-butylamine, bis(4-aminophenyl)methane, bis (4-aminophenyl) sulphone, and bis(4-methylaminophenyl) methane. Other poly(N-glycidyl) compounds that may be used include triglycidyl isocyanurate, N,N'-diglycidyl derivatives of cyclic alkylene ureas such as ethylene urea and 1,3-propylene urea, and N,N'-diglycidyl derivatives of hydantoins such as 5,5-dimethylhydantoin.

Epoxy reactive diluents obtained by the epoxidation of cyclic and acrylic polyolefins may also be employed, such as vinylcyclohexene dioxide, limonene dioxide, dicyclopentadiene dioxide, 3,4-epoxydihydrodicyclopentadienyl glycidyl ether, the bis(3,4-epoxydihydrodicyclopentadienyl) ether of ethylene glycol, 3,4-epoxycyclohexylmethyl 3,4'-epoxycyclohexanecarboxylate or its 6,6'-dimethyl derivative, the bis(3,4-epoxycyclohexanecarboxylate) of ethylene glycol, the acetal formed between 3,4-epoxycyclohexanecarboxyaldehyde and 1,1-bis(hydroxymethyl)-3,4-epoxycyclohexane, bis(2,3-epoxycyclopentyl)ether, butadiene diepoxide or copolymers of butadiene with ethylenic compounds such as styrene and vinyl acetate, epoxidized linoleic acid derivatives and epoxidized polybutadiene.

According to another embodiment, the reactive diluent may be a methacrylic resin monomer or prepolymer, or a nonfunctional or multifunctional acrylate or methacrylate resin monomer. Examples include vinyl, acrylate, styrenic, diene, methacrylate, allyl, acrylamide, methacrylamide, acrylonitrile, and methacrylonitrile containing moieties and combinations thereof. Representative examples include styrene, alpha-methylstyrene, substituted styrene, vinyl ester, vinyl ether, cyclohexyl vinyl ether, N-vinyl-2-pyrrolidone, (meth)acrylamide, N-substituted (meth)acrylamide, octyl (meth)acrylate, nonylphenol ethoxylate(meth)acrylate, isononyl(meth)acrylate, isobornyl(meth)acrylate. 2-(2-ethoxyethoxy)ethyl(meth)acrylate, 2-ethylhexyl(meth)acrylate, lauryl(meth)acrylate, beta-carboxyethyl(meth)acrylate, isobutyl(meth)acrylate, 2-hydroxyethyl(meth)acrylate, (meth)acrylonitrile, maleic anhydride, itaconic acid, isodecyl(meth)acrylate, dodecyl(meth)acrylate, n-butyl(meth) acrylate, methyl(meth)acrylate, hexyl(meth)acrylate, (meth) acrylic acid, N-vinylcaprolactam, N-vinylformamide, stearyl(meth)acrylate, hydroxy functional caprolactone ester (meth)acrylate, isooctyl(meth)acrylate, hydroxyethyl(meth) acrylate, hydroxymethyl(meth)acrylate, hydroxypropyl (meth)acrylate, hydroxyisopropyl(meth)acrylate, hydroxybutyl(meth)acrylate, hydroxyisobutyl(meth)acrylate, tetrahydrofurfuryl(meth)acrylate and combinations thereof.

In one embodiment, the reactive diluent is a monofunctional acrylate, for example, 2-(2-oxy)ethyl acrylate, 2-phenoxy ethyl acrylate, hydroxyl ethyl acrylate, other long chain alkyl acrylates, isobornyl acrylate, cyclic trimethylol propane formal acrylate, monofunctional aliphatic urethane acrylates and combinations thereof.

In a further embodiment, the reactive diluent is a polyacrylate. Examples of polyacrylate reactive diluents include ethylene glycol di(meth)acrylate, hexanediol di(meth)acrylate, triethylene glycol di(meth)acrylate, tetraethylene glycol di(meth)acrylate, dipropylene glycol di(meth)acrylate, trimethylolpropane tri(meth)acrylate, ethoxylated trimethylolpropane tri(meth)acrylate, glycerol tri(meth)acrylate, pentaerythritol tri(meth)acrylate, pentaerythritol tetra(meth) acrylate, tris(2-hydroxyl-ethyl)isocyanurate triacrylate ditrimethylolpropane tetra(meth)acrylate, and alkoxylated polyol derived di- or polyacrylates, such as propoxylated neopentyl glycol diacrylate or propoxylated glycol triacrylate, neopentyl glycol di(meth)acrylate and combinations thereof.

In yet another embodiment, the reactive diluent is a diacrylate such as 1,6-hexanediol diacrylate, 1,9-nonanediol diacrylate, 1,4-butanediol diacrylate, tricyclodecane dimethanol diacrylate, cyclohexane dimethanol diacrylate, alkoxylated cyclohexane diacrylate and tripropylene glycol diacrylate. In a further embodiment, the reactive diluent includes propoxylated neopentyl glycol diacrylate and tripropylene glycol diacrylate.

In yet another embodiment, the reactive diluent may be allyl phenyl ether, 2-allyl phenyl ether, 2-allyl phenol, allyl phenol novolac resin, eugenol, diallyl bisphenol A or triallyl cyanurate.

In still another embodiment, the reactive diluent is selected from an allyl glycidyl ether, an acrylic acid glycidyl ether, a methacrylic acid glycidyl ether, a partially acrylated epoxy, a partially acrylated epoxy, and a mixture thereof.

In some embodiments, the reactive diluent may be included in the curable composition in an amount in the range of between about 1% by weight to about 40% by weight, based on the total weight of the curable composition. In another embodiment, the reactive diluent may be included in the curable composition in an amount in the range of between about 5% by weight to about 30% by weight, based on the total weight of the curable composition. In still another embodiment, the reactive diluent may be included in the curable composition in an amount greater than about 1% by weight, and in other embodiments greater than about 5% by weight based on the total weight of the curable composition. In still further embodiments, the reactive diluent may be included in the curable composition in an amount of less than about 40% by weight, and in still further embodiments less than about 30% by weight based on the total weight of the curable composition.

In another embodiment, the curable composition contains a soluble polyimide. The soluble polyimide of the present disclosure is derived from (i) a phenylindane diamine and (ii) a phenylindane dianhydride and/or a dianhydride. In particular, the soluble polyimide contains recurring units of the formula (4):

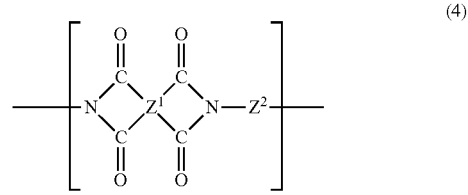

where the four carbonyl groups are bonded to different carbon atoms and are in the ortho or para position to each other so that five or six membered imide rings are formed; $Z^1$ is a tetravalent radical containing at least one aromatic ring, wherein the carbonyl groups are attached to the ring; and $Z^2$ is a divalent organic radical selected from aromatic, aliphatic, alkylaromatic, cycloaliphatic and heterocyclic radicals, combinations thereof, and residues with heteroatom-containing bridging groups where the heteroatom in the bridge is oxygen, sulfur, nitrogen, silicon or phosphorus.

These soluble polyimides are further described in U.S. Pat. No. 3,856,752, the entire contents of which are incorporated herein by reference.

In one embodiment the soluble polyimide contains recurring units of the formula (4) in which $Z^1$ is a phenylindane radical of the formula (5):

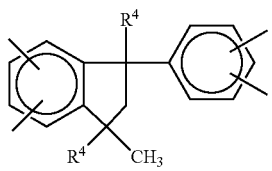
(5)

where $R^4$ is hydrogen or a $C_1$-$C_5$ alkyl group; and $Z^2$ is a phenylindane radical of the formula (6):

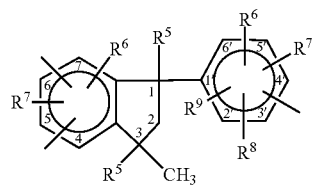
(6)

where $R^5$ is hydrogen or a $C_1$-$C_5$ alkyl group and $R^6$, $R^7$, $R^8$ and $R^9$ are each independently hydrogen, halogen or a $C_1$-$C_4$ alkyl group.

The phenylindane diamine component of the soluble polyimide may be composed of any combination of isomers or substituted isomers of formula (6). The phenylindane diamine component may, for example, contain from 0 wt. % to 100 wt. % of 5-arnino-1-(4'-arninophenyl)-1,3,3-trimethylindane in combination with 100 wt. % to 0% wt. % of 6-amino 1-(4'-aminophenyl)-1,3,3-trimethylindane. Furthermore, one or both of these isomers can be substituted over the entire range from 0 wt. % to 100 wt. % by any of the substituted diamino isomers of formula (6). Examples of such substituted diamino isomers are 5-amino-6-methyl-1-(3'-amino-4'-methylphenyl)-1,3,3-trimethylindane,
5-amino-1-(4'-amino-Ar',Ar'-dichlorophenyl)-Ar, Ar-dichloro-1,3,3-trimethylindane, 6-amino-1-(4'-amino-Ar',Ar'-dichlorophenyl)-Ar, Ar-dichloro-1,3,3-trimethylindane,4-amino-6-methyl-1-(3'-amino-4'-methylphenyl)-1,3,3-trimethylindane and Ar-amino-1-(Ar'-amino-2',4'-dimethylphenyl)-1,3,3,4,6-pentamethylindane where the prefixes Ar and Ar' in the above-mentioned compounds indicate indefinite positions for the given substituents in the phenyl rings.

Among the phenylindane diamines of formula (6) that are preferred in one embodiment are those in which $R^5$ is hydrogen or methyl, $R^6$ and $R^7$ are independently hydrogen, methyl, chlorine or bromine, and $R^8$ and $R^9$ are independently hydrogen, chlorine or bromine. In another embodiment, $R^5$ is hydrogen or methyl, $R^6$ and $R^7$ are independently hydrogen, methyl, chlorine or bromine, and $R^8$ and R are independently hydrogen, chlorine or bromine, and the amino groups are at position 5, 6 or 7 and at position 3' or 4'. In a further embodiment, $R^5$ is hydrogen or methyl, $R^6$, $R^7$, $R^8$ and $R^9$ are hydrogen, and the amino groups are at position 5 or 6 and at position 4'.

In another embodiment, $Z^2$ is a group having the formula (7):

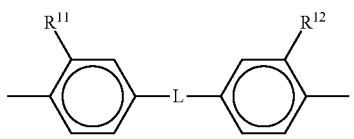
(7)

where L is a covalent bond, methylene, sulfur, oxygen or sulfone; and $R^{11}$ and $R^{12}$ are independently hydrogen, halogen, a $C_1$-$C_5$ alkyl group or a group having the formula

where $R^{13}$ is hydrogen, halogen or a $C_1$-$C_5$ alkyl group.

In one embodiment, the phenylindane dianhydride is a compound having the formula (8):

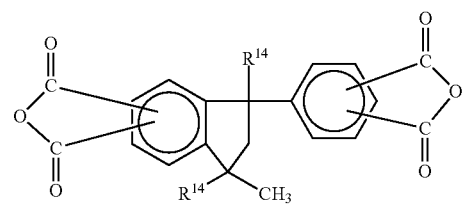
(8)

where $R^{14}$ is hydrogen or a $C_1$-$C_5$ alkyl group. Examples of such dianhydrides include 1-(3',4'-dicarboxyphenyl)-1,3,3-trimethylindane-5,6-dicarboxylic acid dianhydride, 1-(3',4'-dicarboxyphenyl)-1,3,3-trimethylindane-6,7-dicarboxylic acid dianhydride, 1-(3',4'-dicarboxyphenyl)-3-methylindane-5,6-dicarboxylic acid dianhydride and 1-(3',4'-dicarboxyphenyl)-3-methylindane-6,7-dicarboxylic acid dianhydride.

Other dianhydrides which may be combined with phenylindane dianhydride or used by themselves are compounds characterized by the formula (9):

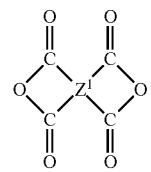
(9)

where the tetravalent radical

is defined above.

In one embodiment, preference is given to aromatic dianhydrides in which the carbon atoms of each pair of carbonyl groups are directly attached at the ortho or para carbon atoms in the $Z^1$ group to provide the following five- or six-membered rings:

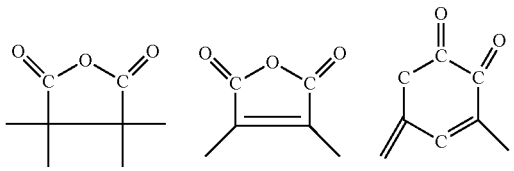

Specific examples of dianhydrides which may be used include 2,3,9,10-perylene tetracarboxylic acid dianhydride, 1,4,5,8-naphthalene tetracarboxylic acid dianhydride, 2,6-di-chlornaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, 2,3,3',4'-benzophenonetetracarboxylic acid dianhydride, pyromellitic dianhydride, 3,3',4,4'-benzophenonetetracarboxylic acid dianhydride, 2,2',3,3'-benzophenonetetracarboxylic acid dianhydride, 3,3',4,4'-biphenyltetracarboxylic acid dianhydride, 2,2',3,3'-biphenyltetracarboxylic acid dianhydride, 4,4'-isopropylidenediphthalic dianhydride, 3,3'-isopropylidenediphthalic dianhydride, 4,4'-oxydiphthalic dianhydride, 4,4'-sulfonyldiphthalic dianhydride, 3,3'-oxydiphthalic dianhydride, 4,4'-methylenediphthalic dianhydride, 4,4'-thiodiphthalic dianhydride, 4,4'-ethylidenediphthalic dianhydride, 2,3,6,7-naphthalenetetracarboxylic acid dianhydride, 1,2,4,5-naphthalenetetracarboxylic acid dianhydride, 1,2,5,6-naphthalenetetracarboxylic acid dianhydride, benzene-1,2,3,4-tetracarboxylic acid dianhydride, pyrazine-2,3,5,6-tetracarboxylic acid dianhydride and thiophene-2,3,4,5-tetracarboxylic acid dianhydride.

In one specific embodiment, the soluble polyimide is a high molecular weight compound prepeared by reacting 5(6)-amino-1(4'-aminophenyl)1,1,3-trimethylindande (BAPI) with benzophenone tetracarboxylic acid dianhydride (BTDA) as described in U.S. Pat. No. 3,856,752. This soluble polyimide is commercially available from Huntsman Advanced Materials Americas LLC under the MATRIMID® brand, for example, MATRIMID® 5218 and 9725 polyimides.

According to one embodiment, the soluble polyimide may be included in the curable composition in an amount in the range of between about 0.1% by weight to about 25% by weight, based on the total weight of the curable composition. In another embodiment, the soluble polyimide may be included in the curable composition in an amount in the range of between about 1% by weight to about 20% by weight, based on the total weight of the curable composition. In still further embodiments, the soluble polyimide may be included in the curable composition in an amount greater than about 0.1% by weight, and in further embodiments greater than about 0.5% by weight, and even in further embodiments at least 1% by weight, based on the total weight of the curable composition. In yet another embodiment, the soluble polyimide may be included in the curable composition in an amount less than about 25% by weight, and in other embodiments less than about 20% by weight, and even in further embodiments less than about 15% by weight, based on the total weight of the curable composition.

In another embodiment, the curable composition may optionally contain one or more additives. Examples of such additives, include, but are not limited to, an additional toughener, catalyst, reinforcing agent, filler, adhesion promoter, flame retardant, thixotrope and mixtures thereof.

Examples of additional tougheners which may be used include copolymers based on butadiene/acrylonitrile, butadiene/(meth)acrylic acid esters, butadiene/acrylonitrile/styrene graft copolymers ("ABS"), butadiene/methyl methacrylate/styrene graft copolymers ("MBS"), poly(propylene) oxides, amine-terminated butadiene/acrylonitrile copolymers ("ATBN") and hydroxyl-terminated polyether sulfones, such as PBS 5003P toughener, commercially available from Sumitomo Chemical Company or RADEL® tougheners from Solvay Advanced Polymers, LLC, core shell rubber and polymers, such as PS 1700 toughener, rubber particles having a core-shell structure in an epoxy resin matrix such as MX-120 resin from Kaneka Corporation, GENIOPEARL® M23A resin from Wacker Chemie GmbH, rubber-modified epoxy resin, for instance an epoxy-terminated adduct of an epoxy resin and a diene rubber or a conjugated diene/nitrile rubber, and high molecular weight polyetherimides such as ULTEM® 2000 product, Blendex 338 product and SILTEM™ STM 1500 product.

Examples of catalysts which may be used include phenolic compounds and derivatives thereof, strong acids such as alkylenic acids, cationic catalysts such as metal halides, organometallic derivatives, metallophorphyrin compounds such as aluminum phthalocyanine chloride, methyl tosylate, methyl triflate, and triflic acid, and oxyhalides. In one embodiment, the catalyst is a phenolic compound, such as phenol, o-cresol, o-, m- or p-dihydroxybenzene, 2,4,6-trinitrophenol, 2,6-di-t-butyl-p-cresol-hydroxybenzene, 2,2'-dihydioxybiphenol, bisphenol-A, bisphenol-F, bisphenol-S, and 4,4-thiodiphenol. In another embodiment, the catalyst is an acid, such as acetic acid, propionic acid, oxalic acid, adipic acid, sebacic acid, benzoic acid, sulfuric acid, p-toluene sulfonic acid, phosphoric acid or thiodipropionic acid.

Examples of fillers and reinforcing agents which may be used include silica, silica nanoparticles pre-dispersed in epoxy resins, coal tar, bitumen, textile fibres, glass fibres, asbestos fibres, boron fibres, carbon fibres, mineral silicates, mica, powdered quartz, hydrated aluminum oxide, bentonite, wollastonite, kaolin, aerogel or metal powders, for example aluminium powder or iron powder, and also pigments and dyes, such as carbon black, oxide colors and titanium dioxide, light weight microballoons, such as cenospheres, glass microspheres, carbon and polymer microballoons, fire-retarding agents, thixotropic agents, flow control agents, such as silicones, waxes and stearates, which can, in part, also be used as mold release agents, adhesion promoters, antioxidants and light stabilizers, the particle size and distribution of many of which may be controlled to vary the physical properties and performance of the curable compositions.

If present, the additive(s) may be added to the curable composition in an amount in the range of between about 0.1% by weight to about 40% by weight, based on the total weight of the curable composition. In further embodiments, the additive(s) may be added to the curable composition in an amount in the range of between about 1% by weight to about 30% by weight, and in still further embodiments between about 5% by weight to about 15% by weight, based on the total weight of the curable composition.

The curable composition according to the present disclosure may be prepared by methods known, for example, by combining the berizoxazine, reactive diluent, soluble polyimide and optional additives with the aid of known mixing units such as kneaders, stirrers, rollers, in mills or in dry mixers. Because benzoxazines are capable of homopolymerization upon heating making them sensitive to high processing temperatures that are generally required to melt and dissolve other additives present, according to some embodiments, the reactive diluent and soluble polyimide may be combined first and used to dissolve any additives present before the benzoxazine is added. Thus, in one embodiment, there is provided a process for producing a curable composition comprising (a) mixing a soluble polyimide with a reactive diluent and optional additive(s) to produce a homogeneous solution or dispersion; and (b) mixing a benzoxazine with the homogenous solution or dispersion to form the curable composition.

It has been surprisingly found that the benzoxazine, reactive diluent and soluble polyimide of the present disclosure, when combined, form a curable composition that, upon curing, produces a cured article that exhibits an excellent balance of thermal, mechanical and physical properties, such as, high glass transition temperature ($T_g$), high toughness, high mechanical strength, high hydrolytic stability and flame retardancy.

Thus, according to one particular embodiment, the curable composition, upon curing, provides an article having a glass transition temperature (as determined by dynamic mechanical analysis or "DMA") of greater than about 180° C. In other embodiments, the curable composition, upon curing, provides an article having a glass transition temperature (as determined by DMA) of greater than about 200° C., and in further embodiments greater than about 210° C., and even further embodiments greater than about 220° C. In other embodiments, the curable composition, upon curing, provides an article exhibiting a fracture toughness G1c (critical rate of release of strainer energy) of greater than about 200 J/m2, and in further embodiments greater than about 225 J/m2. In still other embodiments, the curable composition, upon curing, provides an article exhibiting a dry flexural modulus E' value in dry conditions of greater than about 4000 MPa and greater than 80% retention of dry flexural modulus E' when measured at 120° C. In yet another embodiment, the curable composition, upon curing, provides an article having excellent hydrolytic stability as shown by: a water uptake (i.e. weight gain) of less than 3.0% after immersion in 75° C. water for at least 21 days; and/or a less than 5% loss in strength after exposure to boiling water for about 48 hours.

The curable composition may be cured at elevated temperature and/or pressure conditions to form cured articles. Curing can be carried out in one or two or more stages, the first curing stage being carried out at a lower temperature and then post-curing at a higher temperature(s). In one embodiment, curing may be carried out in one or more stages at a temperature within the range of about 30° C.-300° C., in other embodiments in the range of about 140° C.-220° C. The rate of cure may range from about 30 minutes to 6 hours.

As noted above, the curable composition is particular suitable for use as a coating, adhesive, sealant, and matrice for the preparation of reinforced composite material, such as prepregs and towpegs, and can also be used in injection molding or extrusion processes.

Thus, in another embodiment, the present disclosure provides an adhesive, sealant, coating or encapsulating system for electronic or electrical components comprising the curable composition of the present disclosure. Suitable substrates on which the coating, sealant, adhesive or encapsulating system comprising the curable composition may be applied and heated to cure include metal, such as steel, aluminum, titanium, magnesium, brass, stainless steel, galvanized steel; silicates such as glass and quartz; metal oxides; concrete; wood; electronic chip material, such as semiconductor chip material; or polymers, such as polyimide film and polycarbonate. The adhesive, sealant or coating comprising the curable composition may be used in a variety of applications, such as in industrial or electronic applications.

In another embodiment, the present disclosure provides a cured product comprising bundles or layers of fibers infused with the curable composition.

In yet another embodiment, the present disclosure provides a method for producing a prepreg or towpreg including the steps of (a) providing a bundle or layer of fibers; (b) providing a curable composition of the present disclosure; (e) joining the bundle or layer of fibers and curable composition to form a prepreg or towpreg assembly; (d) optionally removing excess curable composition from the prepreg or towpreg assembly; and (e) exposing the prepreg or towpreg assembly to elevated temperature and/or pressure conditions sufficient to infuse the bundle or layer of fibers with the curable composition and form a prepreg or towpreg.

In some embodiments, the bundle or layer of fibers may be constructed from unidirectional fibers, woven fibers, chopped fibers, non-woven fibers or long, discontinuous fibers. The fibers may be selected from glass, such as S glass, S2 glass, E glass, R glass, A glass, AR glass, C glass, D glass, ECR glass, glass filament, staple glass, T glass and zirconium glass, carbon, polyacrylonitrile, acrylic, aramid, boron, polyalkylene, quartz, polybenzimidazole, polyetherketone, polyphenylene sulfide, poly p-phenylene benzobisoxazole, silicon carbide, phenolformaldehyde, phthalate and naphthenoate.

The curable composition (and prepregs or towpregs prepared therefrom) are particularly useful in the manufacture and assembly of composite parts for aerospace and automotive applications, bonding, of composite and metal parts, core and core-fill for sandwich structures and composite surfacing.

EXAMPLES

Comparative Example 1

70 grams of bisphenol A benzoxazine resin (XU 35610 resin from Huntsman Advanced Materials Americas LLC) was dissolved in 30 grams of an epoxy reactive diluent (Araldite® CY-179 resin from Huntsman Advanced Materials Americas LLC) at 100° C. for approximately 30 minutes to obtain a homogenous solution.

Comparative Example 2

A homogeneous solution was prepared as described in Comparative Example 1 with the exception that 10 grams of CTBN 1300×8 rubber was also added and mixed to obtain a homogeneous solution.

Comparative Example 3

A homogeneous solution was prepared as described in Comparative Example 1 with the exception that 10 grams of ATBN 1300×16 rubber was also added and mixed to obtain a homogeneous solution.

Example 4

5 grams of soluble polyimide (Matrimid® 9725 polyimide) was dissolved in 30 grams of an epoxy reactive diluent (Araldite® CY-179 resin) at 130° C. for 30 minutes to obtain a homogeneous solution ("pre-mix"). 70 grams of bisphenol A benzoxazine resin (XU 35610 resin) was then dissolved in the pre-mix at 130° C. for about 30 minutes to obtain a homogeneous solution.

Example 5

A homogeneous solution was prepared as described in Example 4 with the exception that 7 grams of soluble polyimide (Matrimid® 9725 polyimide) was used instead of 5 grams.

Each of the homogeneous solutions were further mixed under vacuum at a temperature of about 130° C. for about 15-30 minutes. The solutions were then transferred to a pre-heated (150° C.) glass mould containing 0.125 inch Teflon® spacers, and cured for 2 hours at 180° C. and then for 2 hours at 200° C. and finally for 2 hours at 220° C. The cured articles were tested using differential scanning calorimetry (10° C./min heating rate) and dynamic mechanical analysis (5° C./min heating rate) to determine $T_g$, onset and storage modulus values. In addition, the cured articles were subjected to a 75° C. water immersion test for 21 days to determine the % weight gain and subjected to boiling water for 48 hours to determine loss in strength:

TABLE 1

|  | Comp. Ex. 1 | Comp. Ex. 2 | Comp. Ex. 3 | Ex. 4 | Ex. 5 |
|---|---|---|---|---|---|
| Benzoxazine | 70 g | 70 g | 70 g | 70 g | 70 g |
| Epoxy React. Diluent | 30 g | 30 g | 30 g | 30 g | 30 g |
| Soluble Polyimide |  |  |  | 5 g | 7 g |
| CTBN |  | 10 g |  |  |  |
| ATBN |  |  | 10 g |  |  |
| DSC, onset (° C.) | 216.4 | 216.2 | 195.3 | 219.2 | 218.4 |
| DSC, peak (° C.) | 238.2 | 239.6 | 228.4 | 242.2 | 238.8 |
| DSC, enthalpy (J/g) | 435.4 | 373.1 | 416.7 | 402.9 | 325.2 |
| DSC, Tg (° C.) | 236.5 | 235.1 | 225.5 | 236.9 | 235.0 |
| DSC, enthalpy (J/g) | 12.7 | 8.7 | 3.1 | 11.6 | 22.1 |
| % Cure | 94.6 | 98.5 | 96.3 | 95.1 | 90.7 |
| Water uptake, 21 days at 75° C. (% wt. gain) | 2.08 | 2.83 | 2.85 | 2.69 | 2.90 |
| DMA Storage Modulus, Tg (° C.) | 236.0 | 225.8 | 219.9 | 229.7 | 238.0 |
| Storage Modulus at 30° C. (MPa) | 4152 | 2897 | 3207 | 3944 | 3600 |
| Storage Modulus at 121° C. (MPa) | 3484 | 2452 | 2622 | 3254 | 3100 |
| Storage Modulus at 121° C. % retention v. Comp. Ex. 1 48 Hour Boiling Water | — | 70.3 | 75.3 | 93.4 | 89.0 |
| DMA Storage Modulus (MPa) | 193.4 | 188.7 | 182.1 | 193.8 | 196.7 |
| Storage Modulus at 121° C. (MPa) | 3278 | 2263 | 2407 | 3265 | 3138 |
| Storage Modulus at 121° C. % retention v. Comp. Ex. 1 | — | 69.0 | 73.4 | 99.6 | 95.7 |

Flexural strength and modulus for each cured article was also determined in accordance with ASTM D 790 and the $K_{1c}$ and $G_{1c}$ values were determined in accordance with ASTM D5045-96:

TABLE 2

|  | Comp. Ex. 1 | Comp. Ex. 2 | Comp. Ex. 3 | Ex. 4 | Ex. 5 |
|---|---|---|---|---|---|
| Benzoxazine | 70 g | 70 g | 70 g | 70 g | 70 g |
| Epoxy React. Diluent | 30 g | 30 g | 30 g | 30 g | 30 g |
| Soluble Polyimide |  |  |  | 5 g | 7 g |
| CTBN |  | 10 g |  |  |  |
| ATBN |  |  | 10 g |  |  |
| Flex. Strain, % | 2.1 | 3.6 | 3.5 | 4 | 3.5 |
| Flex. Strength (MPa) | 112 | 136 | 135 | 168 | 146 |
| Flex. Modulus (MPa) | 4483 | 3517 | 3807 | 4586 | 4538 |
| Flex. Modulus % retention v. Comp. Ex. 1 | — | 78.4 | 84.9 | 102.3 | 101.2 |
| Tensile Elong., % | 1.6 | 2.0 | 3.0 | 2.0 | 1.5 |
| Tensile Strain (MPa) | 66 | 71 | 84 | 78 | 59 |
| Tensile Modulus (MPa) | 5731 | 3717 | 3173 | 4331 | 4124 |
| Tensile Modulus % retention v. Comp. Ex. 1 | — | 64.9 | 55.4 | 75.6 | 72.0 |
| Fracture Toughness, $G_{Ic}$ (J/m²) | 109.0 | 210.0 | 286.0 | 232.0 | 224.0 |
| Fracture Toughness, $K_{Ic}$ | 0.55 | 0.77 | 0.84 | 0.79 | 0.80 |

Comparing the results in Table 1, it can be seen that the $T_g$ of Examples 4 and 5 did not change appreciably from that of the control Comparative Example 1. However, the $T_g$ of Example 4 is slightly better than those of Comparative Examples 2 and 3 while the $T_g$ of Example 5 is the about the same or slightly better than those of Comparative Examples 2 and 3. It can also be seen that the retention of strength as measured by DMA Storage Modulus is clearly superior to those for Comparative Examples 2 and 3. This is demonstrated when tested at 30° C., 121° C. and 121° C. after exposure to 48 hours of boiling water.

Comparing the results in Table 2, it is clear that the soluble polyimide examples (Examples 4 and 5) retain tensile and flexural properties at a much higher level than either Comparative Examples 2 or 3. Moreover, it is noteworthy that the retention of flexural modulus for Examples 4 and 5 is slightly higher than that for Comparative Example 1. Additionally, the fracture toughness $G_{1c}$ for Examples 4 and 5 increased two-fold as compared to that for Comparative Example 1.

Referring to Tables 1 and 2, it can be seen that the curable compositions according to the present disclosure, when cured, exhibit: 1) high toughness as measured by fracture toughness $G_{1c}$ (i.e. critical rate of release of strain energy) of greater than 200 J/m², especially great than 225 J/m²; 2) a glass transition temperature $T_g$ of greater than 180° C., especially greater than 200° C.; 3) high strength as measured by dry flexural modulus E' values of greater than 4000 MPa in dry conditions and greater than 80% retention of dry flexural modulus E' when measured at 120° C.; and 4) excellent hydrolytic stability as measured by hot water immersion weight uptake of less than 3.0% and a less than 5% loss in strength.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A curable composition comprising:
   (a) about 40% by weight to about 90% by weight of a benzoxazine;
   (b) about 5% by weight to about 30% by weight of a reactive diluent; and
   (c) a soluble polyimide comprising recurring units of the formula (4)

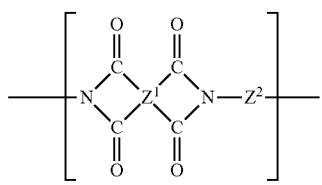

where the four carbonyl groups are bonded to different carbon atoms and are in the ortho or para position to each other so that five or six membered imide rings are formed, $Z^1$ is a phenylindane radical of the formula (5):

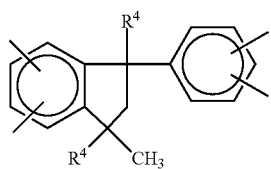

wherein $R^4$ is hydrogen or a $C_1$-$C_5$ alkyl group, and $Z^2$ is a phenylindane radical of the formula (6):

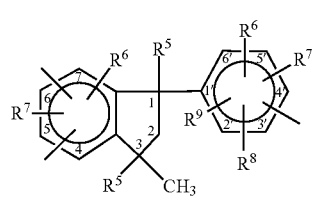

wherein $R^5$ is hydrogen or a $C_1$-$C_5$ alkyl group and $R^6$, $R^7$, $R^8$ and $R^9$ are each independently hydrogen, halogen or a $C_1$-$C_4$ alkyl group and where the percent by weights are based on the total weight of the curable composition.

2. The curable composition of claim 1, wherein the benzoxazine is a compound of the formula (1):

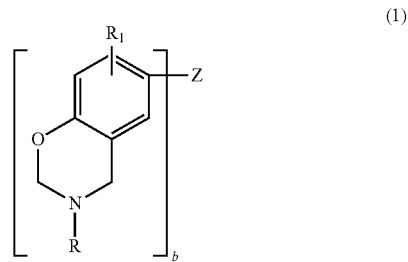

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and when b is 1 Z is a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O, and when b is 2, 3 or 4 Z is a direct bond, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O.

3. The curable composition of claim 2 wherein the benzoxazine is a compound of the formula (1a):

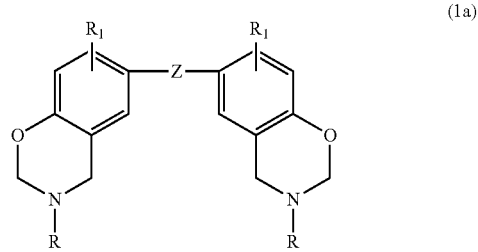

where Z is selected from a direct bond, $CH_2$, $C(CH_3)_2$, C=O, O, S, S=O, O=S=O and

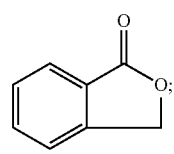

each R is independently hydrogen, a $C_1$-$C_{20}$ alkyl group, an allyl group, or a $C_6$-$C_{14}$ aryl group; and $R_1$ is independently hydrogen, a $C_1$-$C_{20}$ alkyl group, a $C_2$-$C_{20}$ alkenyl group, or a $C_6$-$C_{20}$ aryl group.

4. The curable composition of claim 1 wherein the reactive diluent is an epoxy reactive diluent.

5. The curable composition of claim 4 wherein the epoxy reactive diluent is selected from vinylcyclohexene dioxide, limonene dioxide, dicyclopentadiene dioxide, 3,4-epoxydihydrodicyclopentadienyl glycidyl ether, a bis(3,4-epoxydihydrodicyclopentadienyl) ether of ethylene glycol, 3,4-epoxycyclohexylmethyl 3,4'-epoxycyclohexanecarboxylate, a 6,6'-dimethyl derivative of 3,4-epoxycyclohexylmethyl 3,4'-epoxycyclohexanecarboxylate, a bis(3,4-epoxycyclohexanecarboxylate) of ethylene glycol, an acetal formed between 3,4-epoxycyclohexanecarboxaldehyde and 1,1-bis(hydroxymethyl)-3,4-epoxycyclohexane and bis(2,3-epoxycyclopentyl)ether.

6. The curable composition of claim 1 further comprising one or more of a toughener, a catalyst, a reinforcing agent, a filler, an adhesion promoter, a flame retardant, or a thixotrope.

7. The curable composition of claim 1, wherein the curable composition comprises:
   (a) about 50% by weight to about 80% by weight of the benzoxazine; and
   (c) about 0.1% by weight to about 25% by weight of the soluble polyimide
   where the percent by weights are based on the total weight of the curable composition.

8. A cured article comprising the curable composition of claim 7.

9. The cured article of claim 8 comprising one or more of the following properties:
   (i) a fracture toughness $G_{1c}$ of greater than 200 J/m$^2$;
   (ii) a glass transition temperature $T_g$ of greater than 180° C.;
   (iii) a dry flexural modulus E' of greater than 4000 MPa in dry conditions; and
   (iv) a hydrolytic stability, as measured by immersion in 75° C. water for at least 21 days, of less than 3.0% weight gain.

10. A cured article comprising bundles or layers of fibers infused with the curable composition of claim 7.

11. A method for producing a prepreg or towpreg comprising the steps of (a) providing a bundle or layer of fibers; (b) providing the curable composition of claim 7; (c) joining the bundle or layer of fibers and the curable composition to form a prepreg or towpreg assembly; (d) optionally removing excess curable composition from the prepreg or towpreg assembly; and (e) exposing the prepreg or towpreg assembly to elevated temperature and/or pressure conditions sufficient to infuse the bundle or layer of fibers with the curable composition and form a prepreg or towpreg.

* * * * *